United States Patent [19]

Bryan et al.

[11] Patent Number: 5,098,547
[45] Date of Patent: * Mar. 24, 1992

[54] DISSOLVED OXYGEN SENSOR CALIBRATION, MONITORING AND REPORTING SYSTEM

[76] Inventors: Avron I. Bryan, Cocoa Beach, Fla.; Michael R. Cushman, Kingsport, Tenn.

[*] Notice: The portion of the term of this patent subsequent to Feb. 13, 2007 has been disclaimed.

[21] Appl. No.: 255,504

[22] Filed: Oct. 11, 1988

[51] Int. Cl.$^5$ ............................................. G01N 27/419
[52] U.S. Cl. ..................... 204/401; 204/415; 204/412; 204/153.17
[58] Field of Search ............... 422/83, 90, 94; 324/464; 338/34; 204/401, 411, 415, 153.17, 412

[56] References Cited

U.S. PATENT DOCUMENTS

| | | | |
|---|---|---|---|
| 2,805,191 | 9/1957 | Hersch | 204/431 |
| 4,223,549 | 9/1980 | Mitzinger | 204/401 |
| 4,457,808 | 7/1984 | Taylor et al. | 204/401 |
| 4,460,448 | 7/1984 | Wolcott | 204/401 |
| 4,900,422 | 2/1990 | Bryan et al. | 204/401 |

Primary Examiner—Richard V. Fisher
Assistant Examiner—Todd J. Burns
Attorney, Agent, or Firm—Macdonald J. Wiggins

[57] ABSTRACT

A dissolved oxygen measurement system includes real time monitoring and calibrating of a dissolved oxygen sensor. The sensor includes a pair of measuring electrodes, an electrolyte, and a pair of closely spaced electrolysis electrodes. The housing includes a permeable membrane and is immersed in the process solution. A computer is provided, programmed to perform dissolved oxygen concentration measurement, and continuous monitoring of the membrane impedance and sensor condition. A test electrode is disposed in the process solution adjacent the membrane and is driven by a low level pseudorandom binary signal from the computer producing a current through the membrane impedance which is monitored by the computer. Small pulses of direct current are passed between the electrolysis electrodes, producing small increases in oxygen. The pulse characteristics of the resulting small increases in oxygen concentration are continuously monitored by the computer for any changes in condition of the dissolved oxygen sensor and for on-line recalibration of the sensor and system.

6 Claims, 2 Drawing Sheets

DISSOLVED OXYGEN SENSOR CALIBRATION, MONITORING AND REPORTING SYSTEM

BACKGROUND OF THE INVENTION

1. Field of the Invention

The present invention relates to dissolved oxygen sensors, and more particularly to a dissolved oxygen concentration monitoring system which provides automatic on-line, in place calibration, and failure detection and reporting.

2. Description of the Prior Art

The concentration of oxygen in processes containing water is important in many industrial processes and is critical for processes based on oxygen-using microorganisms; for example, fermentation, recombinant DNA processes, and waste water treatment. The present real time measurement of oxygen in industrial processes utilizes two well known forms of sensors: galvanic (voltage); and amperometric (current). The signal developed by the sensor is in response to the diffusion of gases across the membrane. Specifically, oxygen is reduced at the cathode in the sensor, generating either a potential or current. In either type sensor, the operation of the sensor is maintained such that the signal from the sensor is approximately linearly proportional to the partial pressure of oxygen or the concentration of dissolved oxygen.

There are a number of problems that can occur with this measurement system. For example, the membrane can become coated by the process or can change due to structural failure, such as cracks, leakage or degradation. Within the sensor body, the physical condition of the electrodes and the condition of the electrolyte directly affect the sensor signal current. Changes or degradation of these factors can occur in prior art systems without being detected, resulting in out-of-tolerance processes.

The most costly and error prone activity for any on-line, real time process measuring system is the repeated calibration of the system and sensor to maintain measurement accuracy.

Thus, there is a need for an oxygen measurement system in which defects in the oxygen sensor can be detected in real time on-line and accurate calibrations can be automatically performed on-line, thereby reducing operations cost and the probability of undetected failures which may produce catastrophic results.

SUMMARY OF THE INVENTION

The present invention is a dissolved oxygen measurement system having a real time, on-line capability for testing, monitoring, and calibrating the dissolved oxygen sensor and the system. The system and sensor response to oxygen is detected and analyzed by generating known values of additional oxygen, thus allowing for both automatic self calibration of the sensor, and self testing of the sensor and the system. An independent measurement of the $O_2$ sensor membrane impedance is also performed.

An oxygen sensor having conventional anode and cathode electrodes is provided with two auxiliary electrodes internal to the body of the sensor, and one electrode external to the sensor membrane. In use, the oxygen sensor and external electrode are disposed in the process solution or stream. In addition to the conventional sensor measuring anode and cathode electrodes, two additional electrodes are located in the sensor electrolyte. A controlled current is passed between these two additional electrodes and through the sensor oxygenated electrolyte. The resulting electrolytic action produces small and controlled amounts of extra oxygen. The sensor response to the additional known oxygen increase permits in-place calibration of the sensor.

The internal solution of the oxygen sensor is a well defined volume that is diffusion controlled and, therefore, the addition of known amounts of oxygen into that solution allows for self calibration of the sensor. The periodic generation of a known amount of oxygen provides both recalibration and sensor performance capability. Further, by monitoring the decay of the additional oxygen in the sensor solution as it reaches equilibrium with the process solution, the relative performance of the sensor membrane can be established.

The $O_2$ measurement system is controlled by a computer with appropriate algorithms and additional controlled hardware to perform all of the functions of oxygen measurement, testing and analysis of the sensor and system response. To this end, the signal from the oxygen sensor is applied, to an analog-to-digital (A/D) converter and the digitized signals are input to the computer. The computer processes the signals and converts the results to provide reports on the oxygen concentration in the solution as well as reports on the status of the oxygen sensor.

It is also preferred to include a temperature sensor in the process solution near or within the oxygen sensor. The output of the temperature sensor is converted to digital form which is used by the system computer to compensate the oxygen concentration readings.

Monitoring of the sensor membrane impedance is provided by a low level voltage pseudorandom binary signal applied by the system to an electrode external to the sensor membrane. This signal is less than 0.2 mV and its effect is removed from the dc current or voltage signal produced by the sensor. A current from the test signal will flow from the external impedance anode electrode through the process solution, through the membrane, through the sensor electrolyte and sensor cathode electrode to the measurement system of the computer.

As may now be understood, the pseudorandom current will be flowing in the sensor electrode along with the dc currents generated by the reduction of the oxygen. The test currents will add and subtract from the dc oxygen signal currents. The composite signal is applied via the A/D to the system computer which cross-correlates the composite signal with the known pseudorandom signal and extracts a value proportional to the impedance of the membrane. This impedance can range from several thousand ohms to several megohms as normal operating values. Other impedances in the signal path of the test signal are normally less than 0.1% of the lowest membrane impedance and therefore may be ignored.

To minimize the effects of capacitances in the external electrodes, sensor membrane, internal electrodes, and process solutions, the pseudorandom signal is produced at a low bit rate (such as 1 bit per second). The measurements will thus provide the resistive component of the sensor membrane impedance.

The impedance and permeability estimate of the sensor membrane is compensated for temperature in order to prevent large errors in estimation due to the sensor membrane variation with temperature.

Periodic generation of the additional oxygen signal to calibrate, test and verify the entire measurement system is provided by a computer controlled generator and the two additional internal sensor electrodes used for electrolysis. The system, on a programmable periodic basis, applies a low level constant current or potential across these electrodes. This system test signal is selected for a time period and amplitude level that is appropriate for the sensor internal electrolyte volume and diffusional characteristics, thus generating a known amount of oxygen. The additional oxygen value (over the process solution average concentration of oxygen) is monitored in the normal manner. The system oxygen estimate delivered to users and control systems is maintained at the last average reading before the application of the test and calibration signal.

The system computer, having issued the test signal for oxygen, can now subtract the additional oxygen level signal from the normal level of oxygen in the process solution. System computer algorithms then compare the amplitude and speed of response to the additional oxygen to determine both sensor and system performance. For example, the time and manner of the return of the signal to normal behavior defines the diffusional characteristics of the system. This includes both the membrane and the hydrodynamics of the sensor.

At the time of implementation of the system of installation of a new sensor for the system, the initial membrane impedance estimate, process temperature and the responses to the additional oxygen test signal are measured and stored. Thereafter, the stored values are used as references to compare against the continuous membrane test results and the sensor additional oxygen test results. Changes in the membrane impedance or diffusional characteristic values indicate degradation or failure in this critical part of the sensor. Internal sensor measuring anode and cathode electrode degradation, or change in electrolyte, are indicated by the speed and shape of the response to the additional oxygen test. A failure in some other part of the system is indicated by a lack of response to the known additional oxygen. The measurement system will report on the results of the automatic calibration process and will warn if the sensor or system have failed or the performance thereof has degraded.

As will now be recognized, the system generates reports on:
1. Relative changes in the impedance of the sensor membrane from a selected event such as time of placement in service.
2. Relative changes of the sensor time response to the additional oxygen in the sensor.
3. Recalibration and sensor signal response for the known quantity of additional oxygen.

DETAILED DESCRIPTION OF THE PREFERRED EMBODIMENT

Figure 1:
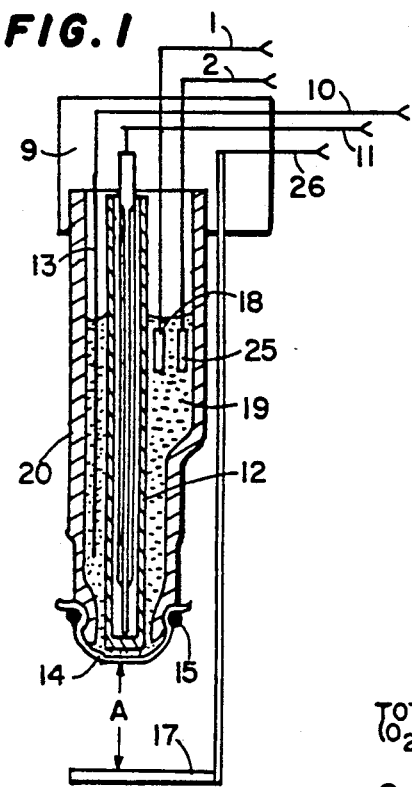
FIG. 1 is a cross sectional view of an oxygen sensor with an external test electrode and a pair of internal electrolysis electrodes in accordance with the invention.

The invention is a system for automatic calibration and monitoring for dissolved oxygen in a process solution. A dissolved oxygen sensor combined with two additional internal electrodes and an external test electrode in the process solution to provide means for calibration, testing, analyzing, and reporting the oxygen sensor status as well as the total system response. Referring to FIG. 1, a dissolved oxygen sensor 8 is mounted to a bracket 9 from which test electrode 17 depends. The dissolved oxygen sensor may be an amperometric or galvanic type. The anode electrode 13 of sensor 8 is preferably formed from silver. The cathode electrode 12 is preferably formed from platinum. $O_2$ measurement electrodes 13 and 12 are disposed in a stainless steel housing 20 having an open lower end. A sensor membrane 14 is formed from Teflon ® covering the open end of housing 20, and is held in place by a rubber "O" ring 15. Test electrode 17 is spaced a distance A from membrane 14. Distance A is not critical but is normally less than 0.5 inches. Test electrode 17 can be of any suitable anode material, such as platinum. Electrolysis electrodes 18 and 25 are disposed in the sensor electrolyte 19 spaced apart a distance of approximately 0.1 inches. Electrode 18 serves as an anode and electrode 25 serves as a cathode and are preferably formed from platinum.

As will be noted, anode electrode 13 of sensor 8 is connected to lead 10, and cathode electrode 12 connects to lead 11. Test electrode 17 is connected to lead 26. Electrolysis electrodes 18 and 25 are connected to leads 1 and 2 respectively.

Figure 2:
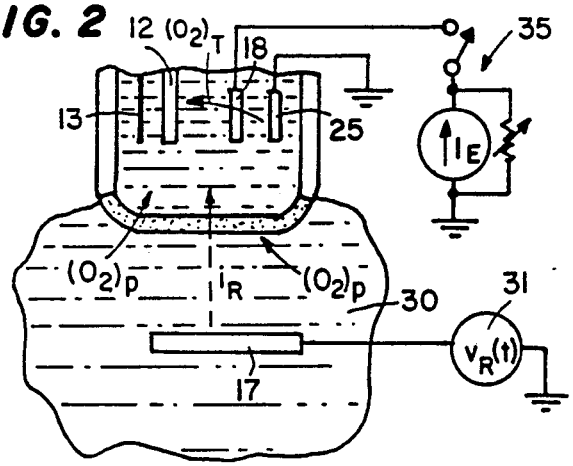
FIG. 2 is a partial view of the sensor and electrodes of FIG. 1 illustrating generation of a test pulse of excess oxygen and the generation of a membrane test signal.

Turning now to FIG. 2, a portion of an operating system is shown with process solution 30. Membrane 14 is indicated with process oxygen $(O_2)P$ incident thereon. The measurement system will normally measure the concentration of such oxygen in solution 30. As will be described in more detail below, a very low amplitude time varying voltage $v_R(t)$ 31 is applied between ground and test electrode 17. A small current $i_R$ will flow through membrane 14 to the $O_2$ measuring cathode electrode 12 and will be proportional to the impedance of membrane 14. Suitable instrumentation, as described hereinafter, will measure this impedance. As will be described below, real time monitoring of this impedance permits an alarm if any change in membrane impedance occurs during operation due to contamination or physical damage.

Figure 3:
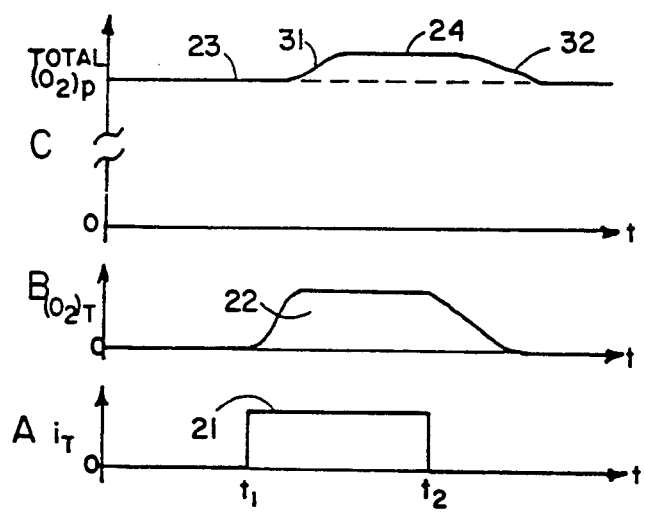
FIG. 3 is a set of waveforms produced in generation of an oxygen pulse.

The calibration of the sensor response to $O_2$ and the condition of the electrodes 12, 13 and electrolyte 19 is monitored by periodically producing a small controlled quantity increase in oxygen concentration within the sensor electrolyte 19. A pulsed variable current source $I_E$ 35 is connected between electrodes 25 and 18 via leads 1 and 2. The current is applied in a short interval $(t_1$ to $t_2)$ as indicated in line A of the waveform diagram of FIG. 3. An electrolysis current $I_E$ will flow, causing electrolysis of the electrolyte 19. The generating current is shaped such that he generation of oxygen at the anode 12 is the preferred electrolysis. The test pulse of oxygen $(O_2)_T$ released within the sensor (indicated in line B) will cause an increase in total process oxygen $(O_2)_P$ as shown in line C. When current $I_E$ is turned off at $t_2$, the excess oxygen will be dispersed from the sensor to the measuring process.

A small increase in the measured value of total oxygen 23 from sensor 8 will occur as shown in line C. The increase is analyzed for amplitude 24, rise time 31, and decay time 32. The initial characteristics of the waveform at implementation are measured and stored. Subsequent measurements during system operation are compared to the initial data. Any physical changes in sensor 8 will affect the sensor's response to the test oxygen pulse and an alarm may be generated if a change is out of preselected thresholds. Automatic recalibration is obtained by varying the electrolysis current $I_E$ to obtain two or more known levels of oxygen thus providing the sensor data for recalibration.

Figure 4:
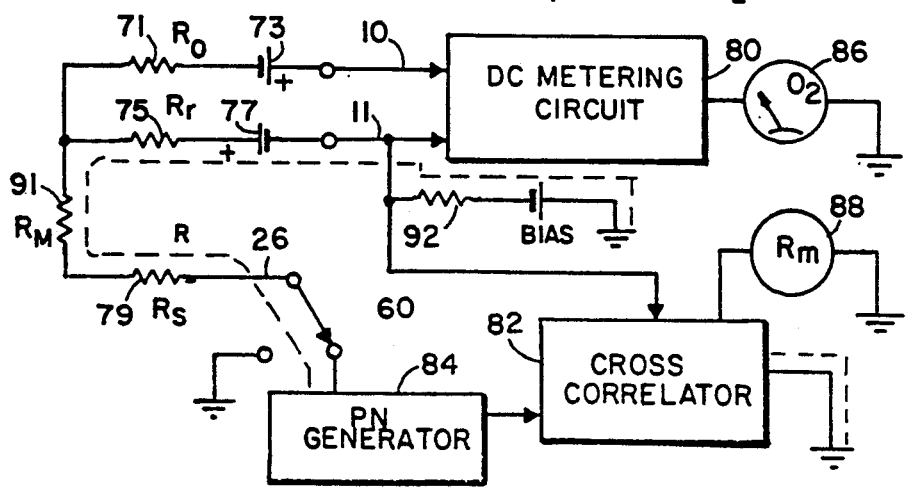
FIG. 4 is an equivalent circuit of a system using the sensor and electrodes of FIG. 1.

The operation of the impedance monitoring system of the invention may best be understood with reference to FIG. 4 in which a simplified functional schematic diagram is shown. The anode electrode 13 of FIG. 1 of oxygen sensor 8 is represented by an equivalent voltage cell 73. The voltage of cell 73 will vary with the concentration of oxygen in the process. An equivalent resistance 71 ($R_o$) is the impedance from electrode 13 of FIG. 1 to membrane 14. An equivalent reference voltage cell 77 represents the electrode 12 of FIG. 1 and its potential is normally constant. The impedance from electrode 12 to membrane 14 is indicated by equivalent resistance 75 ($R_r$).

The anode and cathode electrodes are connected by leads 10 and 11 to a dc metering circuit 80 which compares potential 73 to potential 77 and produces a reading on meter 86 calibrated as the concentration of dissolved oxygen in the process solution. In accordance with the invention, contact is made with the process solution by test electrode 17 which is connected by switch 60 to pseudorandom (PN) signal generator 84 via lead 26. An equivalent solution resistance 79 ($R_S$) is shown which occurs between electrode 17 and membrane 14. An equivalent membrane resistance $R_M$ 91 is shown between the solution resistance $R_S$ 79 and the common point to equivalent resistances $R_r$ 75 and $R_o$ 71. The membrane resistance $R_M$ 91 is at least 10,000 times greater than the sum of $R_S$ and $R_r$ or $R_S$ and $R_o$.

Although not shown, the impedances generally include small capacitances. These do not affect the dc measurement and the PN signal is generated at a low rate, for example, 1 bit per second. Thus, the capacitive reactance is negligible.

The level of the PN signal is low, on the order of 0.2 millivolts and is thus negligible with respect to the biased dc voltage and dc signal voltages which ar typically hundreds of millivolts. Therefore, it has no effect on the oxygen concentration measurement. As will now be recognized, a test current $i_R$ proportional to values of $R_M$ will flow to ground through the bias resistor R 92. The waveform from PN generator 84 provides the reference to cross correlator 82 which extracts the voltage across resistor 92 due to the $i_R$ signal and produces a reading on meter 88 proportional to the membrane resistance $R_M$.

Figure 5:
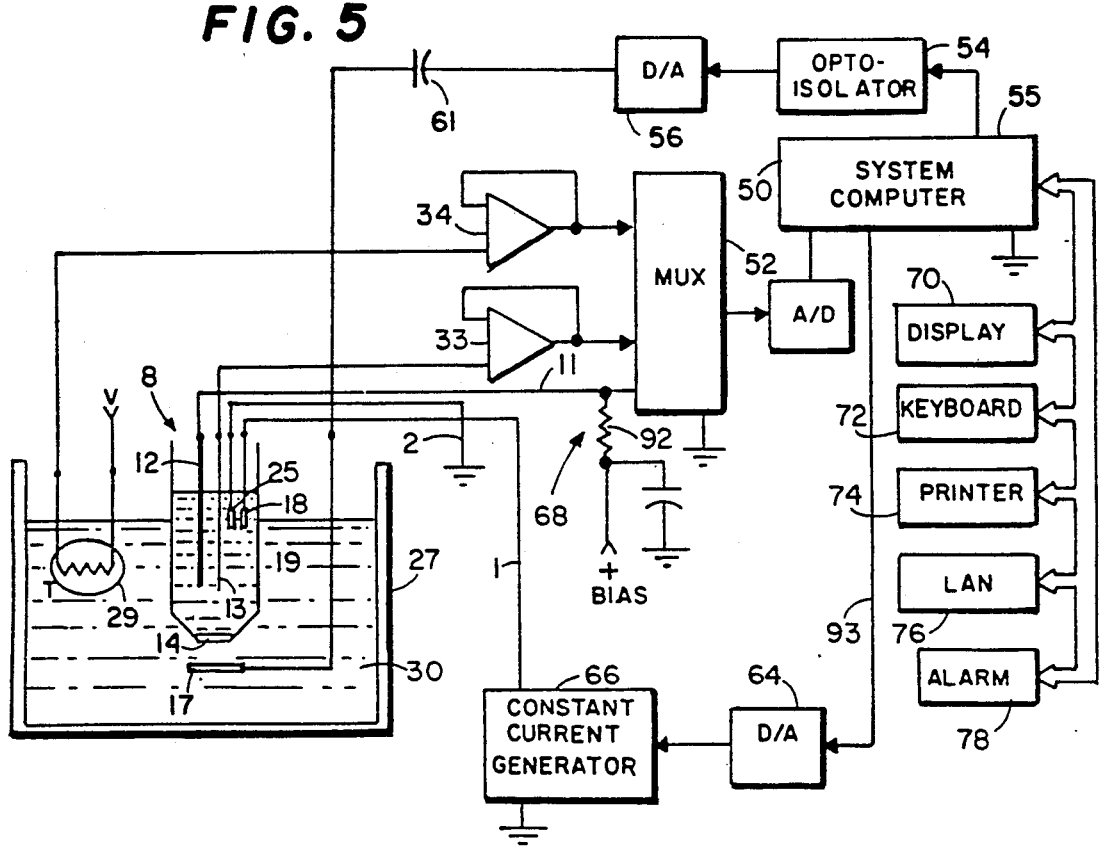
FIG. 5 is a schematic and block diagram of a preferred embodiment of the system of FIG. 4 utilizing a computer for measuring the sensor membrane impedance, and for calibration and testing of the sensor with oxygen pulses.

The preferred implementation of the invention is shown by the schematic and block diagram of FIG. 5. A process solution 30 for which the oxygen concentration is to be measured is shown in a tank 27. A dissolved oxygen sensor 8 is shown immersed in the solution 30. In addition, a temperature sensor 29, which may be of any electrical type, is provided to allow automatic temperature compensation of the dissolved oxygen sensor response and the estimate of the impedance $R_M$ of sensor membrane 14.

A system computer 50 is provided having a number of stored programs. One program is used to generate a pseudorandom signal. As previously discussed, it is desirable that the pseudorandom signal be bimodal at a low frequency such as 1 bit per second. The pseudorandom signal is produced by the system computer 50 on lead 55 and fed to a digital-to-analog (D/A) converter 56 via an optical isolator 54. The test signal is connected to test electrode 17 via blocking capacitor 61 which is used to remove any dc component in the pseudorandom signal. The PN signal will produce an output on lead 10 superimposed on the dc oxygen concentration signal. For monitoring the condition of sensor 8, pulses of excess oxygen are generated as discussed above. A second stored program in the system computer 50 commands a constant current generator 66 via D/A converter 64 to generate an electrolysis current on a programmable periodic basis. Further, the current amplitude and time duration thereof are programmable to accommodate the sensor internal volume and internal solution characteristics and the locations of the test electrolysis electrodes 18 and 25. The current to generate the additional oxygen is applied via lead 1 to the electrolysis electrode 18 and is returned to ground by electrode 25 and lead 2.

Having described the test procedures controlled by computer 50, the operation of the system will now be discussed. The oxygen sensor anode 13 dc output is available via lead 10 to the circuit 33 which is connected to be either an emitter follower or a current-to-voltage converter to accommodate the type of dissolved oxygen sensor 8 in use. Circuit 33 drives a multiplexer (MUX) 52. Temperature sensor 29 provides a voltage signal via emitter follower 34 to MUX 52. The potential of the bias voltage via bias network 68 on the sensor cathode lead 11 is fed directly to MUX 52. Multiplexer 52 has its output connected via an analog-to-digital (A/D) converter 62 to system computer 50.

As previously discussed, the voltage levels of the pseudorandom signals applied to the test electrode 17 are on the order of 0.2 millivolts or less while the biased dc voltages and dc signal voltages are on the order of hundreds of millivolts. Therefore, A/D converter 62 necessarily has a capability of 14 bits.

System computer 50 includes stored programs to perform cross-correlation and statistical analyses on the data contained in the dc signal from the oxygen anode electrode 13 and from test and monitoring signals. As is apparent from the equivalent circuit of FIG. 4, PN current $i_R$ will produce a voltage drop across resistor 92 which is connected to ground through the bias source. This voltage is analyzed by the cross-correlation program to produce an output proportional to the impedance $R_M$ of membrane 14. The programs analyze the response of the sensor to the additional calibration and test oxygen pulse 22 of FIG. 3, and also measure the solution oxygen concentration. Thresholds for all parameters of the sensor 8, and the test and monitoring elements of the system, are programmable and are entered into system computer 50. Whenever any of the programmed thresholds is exceeded, an appropriate alarm 78 is actuated. The process solution oxygen concentration, the sensor membrane impedance, the sensor response time, decay time, calibration parameters and process temperature are available for real time monitoring on the system display 70, printer 74; and a local area network 76.

Calibration of the system may be carried out by entering appropriate keyboard commands via keyboard 72 or via the local area network 76. The system computer program may select new threshold values for the sensor 8 as required and system test and monitoring signals based on the calibration.

ALTERNATIVE EMBODIMENT

Figure 6:
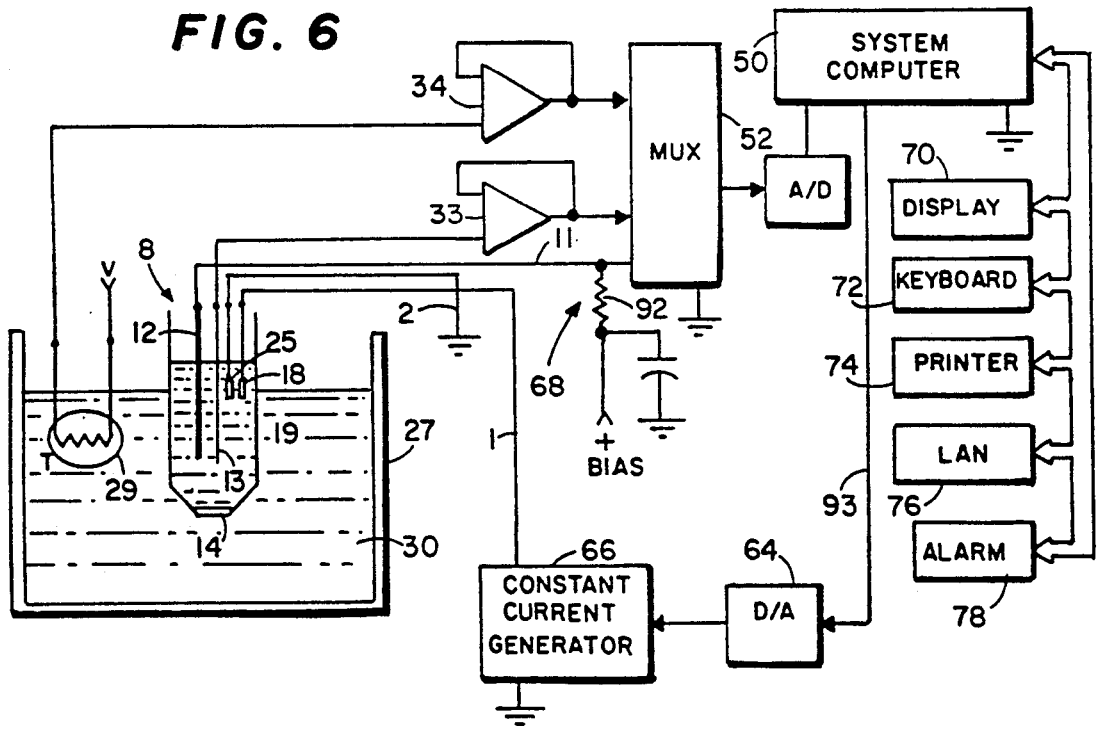
FIG. 6 is an alternative embodiment of the system of FIG. 5 utilizing a computer for calibration and testing the sensor with oxygen pulses.

The use of electrode 17 for monitoring the impedance of sensor membrane 14 and electrodes 18 and 25 for producing oxygen pulses for calibration and monitoring the internal status of sensor 8 in conjunction with computer 50 has been disclosed above. In an alternative embodiment shown in schematic and block diagram form of FIG. 6, electrode 17 is omitted and computer 50 is programmed to periodically enable constant current generator 66 as previously described. The program includes the following functions:

measures dc levels from sensor electrodes 12 and 13;
determines oxygen concentration from dc levels;
displays oxygen concentration;
analyzes amplitude, rise time, decay time and calibration parameters of dc levels produced by periodic oxygen pulses from electrolysis by electrodes 25 and 18;
monitors such amplitude, rise time and decay time of dc levels for any changes therein; and
compares such changes to thresholds and produces alarms when thresholds are exceeded.

With this embodiment, there is no requirement for the program to include a pseudorandom signal generator or cross correlation function.

Although specific illustrations of the preferred embodiment have been presented, these are for exemplary purposes only and various alternative arrangements may be used without departing from the spirit and scope of the invention.

We claim:

1. A test and monitoring system for providing automatic on-line, real-time calibration and monitoring of the condition of a dissolved oxygen sensor comprising:
    (a) said sensor having a housing, an anode electrode, a cathode electrode, an electrolyte, and a permeable membrane, said sensor immersed in a process solution;
    (b) a test electrode immersed in said process solution adjacent said permeable membrane;
    (c) generator means for generating a low level, time varying signal, an output of said generator connected between a system ground and said test electrode for producing a time varying current through said membrane to said cathode electrode, and through a resistor to said system ground;
    (d) means for measuring a voltage drop across said resistor from said time varying current and a dc reference current in which a time varying component is proportional to the impedance of said membrane;
    (e) a pair of electrolysis electrodes disposed within said sensor and immersed in said electrolyte solution in a closely spaced relationship, a first one of said electrolysis electrodes connected to said system ground;
    (f) a pulsed direction current source connected between a second of said pair of electrolysis electrodes and said system ground for producing electrolysis in said sensor electrolyte solution to thereby release a pulse of a predetermined volume of oxygen within said sensor, said oxygen producing a controlled increase in dissolved oxygen relative to dissolved oxygen due to the process, wherein said oxygen sensor produces a voltage pulse, from said dissolved oxygen increase, superimposed on a process oxygen level voltage; and
    (g) means for comparing the rise time, magnitude, and decay time of said oxygen voltage pulse with calibrated values and for detecting deviations from calibrated values indicative of deterioration of said dissolved oxygen sensor.

2. The system as recited in claim 1 in which said time varying signal is a pseudorandom binary signal.

3. The system as recited in claim 2 which further comprises a system computer.

4. The system as recited in claim 3 in which said generator means includes a first program resident in said computer for generating said pseudorandom binary signal, said voltage drop measuring means is a second program resident in said computer for cross correlating said voltage drop with said pseudorandom binary signal to thereby separate said time varying component, and a third program for measuring and displaying a value of said membrane impedance.

5. The system as recited in claim 4 in which said comparing and detecting means includes a fourth program for measuring and storing calibrated values of said rise time, said magnitude, and said decay time of said oxygen voltage pulse, for comparing monitored ones of said oxygen voltage pulses with said calibrated values and displaying deviations from such calibrated values.

6. The system as recited in claim 5 in which said fourth program includes thresholds for said calibrated values and means for enabling alarms when any of the thresholds are exceeded.

* * * * *